United States Patent [19]
Borchert et al.

[11] Patent Number: 6,165,718
[45] Date of Patent: *Dec. 26, 2000

[54] METHOD FOR IN VIVO PRODUCTION OF A MUTANT LIBRARY IN CELLS

[75] Inventors: Torben Vedel Borchert, Jyllinge, Denmark; Stanislas Dusko Ehrlich, Paris, France

[73] Assignee: Novo Nordisk A/S Novo Alle, Bagsvaerd, Denmark

[ * ] Notice: This patent issued on a continued prosecution application filed under 37 CFR 1.53(d), and is subject to the twenty year patent term provisions of 35 U.S.C. 154(a)(2).

[21] Appl. No.: 09/112,410

[22] Filed: Jul. 8, 1998

Related U.S. Application Data

[63] Continuation of application No. PCT/DK97/00014, Jan. 10, 1997.

[30] Foreign Application Priority Data

Jan. 10, 1996 [DK] Denmark .................................. 0018/96

[51] Int. Cl.⁷ .............................. C12Q 1/68; C12N 15/70; C12N 15/63; C12N 9/10; C12N 9/14
[52] U.S. Cl. ............................. 435/6; 435/69.1; 435/471; 435/476; 435/488; 435/320.1; 435/489; 435/252.33; 435/189; 435/193; 435/195
[58] Field of Search ..................................... 435/69.1, 7.1, 435/69.2, 91.4, 455, 471, 476, 483, 484, 485, 487, 488, 320.1, 348, 325, 354, 6, 489, 252.33, 195, 189, 193

[56] References Cited

FOREIGN PATENT DOCUMENTS

WO 90/07576  7/1990  WIPO .

OTHER PUBLICATIONS

James E. Bailey, Science, vol. 252, pp. 1668–1675, Jun. 21, 1991.

*Primary Examiner*—David Guzo
*Attorney, Agent, or Firm*—Elias J. Lambiris; Valeta Gregg

[57] ABSTRACT

A method for in vivo production of a library in cells comprising a multitude of mutated genetic elements, wherein an error-prone polymerase is used in each ancestral cell to replicate all or a part of a genetic element independently of the host chromosomal replication machinery. The genetic element comprises i) an origin of replication from which replication is initiated,
  ii) optionally a genetic marker, e.g. a gene conferring resistance towards an antibiotic,
  iii) a gene encoding the polypeptide of interest.

Also methods for the generation of a DNA sequence encoding a desired variant of a polypeptide of interest, and for the determination of such a DNA sequence are described.

12 Claims, No Drawings

METHOD FOR IN VIVO PRODUCTION OF A MUTANT LIBRARY IN CELLS

CROSS-REFERENCE TO RELATED APPLICATIONS

This application is a continuation of PCT/DK97/00014 filed Jan. 10, 1997, the contents of which are fully incorporated herein by reference.

FIELD OF THE INVENTION

The present invention relates to methods for in vivo production of libraries of polypeptide variants, the screening of these variants and selection of those exhibiting desired properties. The invention furthermore relates to methods for producing the desired polypeptide variants.

BACKGROUND OF THE INVENTION

An increasing number of polypeptides, including enzymes and non-enzymatic proteins, are being produced industrially, for use in various industries, household, food/feed, cosmetics, medicine etc. One of the major sources for these proteins is and have been microorganism found in nature.

The classical approach for finding polypeptides with new and special properties, have been to screen wild type organisms present in nature. This has been a very successful way of procuring polypeptides to be used in such diverse areas as the above mentioned applications.

However, often it has not been possible to produce such polypeptides in sufficient amounts because the quantities produced in the natural host systems were too minute to allow a production, and even if the cost was no problem, difficulties could be encountered in providing sufficient amounts in relation to the demand (e.g. human growth hormone).

Such problems have to a large degree been overcome by the advent of recombinant techniques for the production of polypeptides. In this art polypeptides are produced by the use of biological systems. Genes encoding certain polypeptides are cloned and transferred into cells that will produce the polypeptides in quantities much larger than those, wherein they are produced in the original organism. Over the latest twenty years a large number of methods for the production of polypeptides according to such techniques have been developed.

Often, proteins from natural sources do not meet the requirements for certain applications, and it will be necessary to modify existing proteins towards certain activities or biophysical properties.

It is possible to generate new variants of a protein by classical mutagenesis of the microorganism using radiation (X-ray and UV) or chemical mutagens. However, since this approach is a very labour and time consuming process, in the same last two decades researchers have been developing improvements on existing polypeptides by using more specific and selective recombinant techniques, such as protein and genetic engineering for creating artificial diversity.

Based upon considerations using knowledge of the structure-function relationships and general protein chemistry, researchers have come a long way in designing polypeptide variants exhibiting improvements in various properties.

However, it has also been realised that the various interactions into which polypeptides take part, are so complex that rational design according to such knowledge has serious limitations, and in recent years methods employing random mutagenesis followed by screening of or selection from very large numbers of variants produced therefrom has gained interest.

For this purpose a microbial library of mutants is generated for subsequent expression and screening to determine variants possessing the desired properties.

Over the years many both in vitro and in vivo DNA mutagenesis techniques for creating high numbers of different variants of polypeptides have been developed.

Considering the fact that a typical naturally occurring polypeptide consists of between 100 and 1000 amino acids, and each may be varied in 20 ways (only to stay within the naturally occurring amino acids), the number of possible variants for a specific polypeptide is enormous. Since the main parameter that defines or measures the usefulness of a microbial collection or library used to identify improved variants of polypeptide is the number of different variants, N, which is comprised in the collection, a need for large libraries has emerged.

Especially in cases when a powerful selection system is available, the limiting factor for the identification of the desired polypeptide is the size of the library.

In in vitro systems the practical, state of art, limit for N is about $10^8$. This is mainly due to inefficiency of transformation (introduction of DNA into the cell) of the manipulated DNA into the host organism. This number varies a lot from organism to organism: in the presently best case, *E. coli,* the usual efficiency of transformation of in vitro manipulated DNA, e.g. a ligation of DNA fragments or chemical treatment of DNA, leads at the most to library sizes up to $10^8$ bacteria (Greg Winter, *Current methods in Immunology* 5: 253–255, 1993). Very few examples of libraries of this size have been reported.

In vitro library constructions in other prokaryotes, such as Bacillus sp., Streptococcus sp. or Staphylococcus sp. will for practical reasons be orders of magnitude below this number.

Considering eukaryotic hosts such as *Saccharomyces cerevisiae* or various Aspergillus sp., an even lower number of transformants can be expected from in vitro manipulated DNA.

A special case of a large library has been reported based on in vivo recombination between libraries of antibody light and heavy chains based on a specially designed system useful for that particular case (Griffiths, A. D. et al., 1994, *EMBO J.* 14: 3245–3260).

A number of methods are available to generate variants of a polypeptide in microorganisms in vivo, ranging from very simple, such as treating cells with chemical or physical mutagens, to rather complex, relying on cells that contain an error-prone DNA polymerase but lack the mismatch repair system which corrects the errors (Stratagene, XL1-red (muts, mutD, mutT) Catalog #200129). But these techniques have a major drawback as the mutagenesis is not targeted to a specific part of the genome (coding for the polypeptide of interest) and high frequencies of mutations are generated also in essential genes for the cell as well as in the target gene, resulting in massive cell death, together with a high number of cells, where the mutations do not influence the polypeptide of interest. Such "noise" will limit the accumulation of mutations in the target region.

It is therefore the object of the invention to provide an in vivo target region-specific mutagenesis procedure in order to produce very large numbers, N, of polypeptide variants.

A second object of the invention relates to the screening or selection of variants with the desired properties, both by existing and future technologies.

SUMMARY OF THE INVENTION

The present invention therefore relates to a method for in vivo production of a library in cells comprising a multitude of mutated genetic elements, wherein an error-prone polymerase is used in each ancestral cell to replicate all or a part of a genetic element comprising i) an origin of replication from which replication is initiated, ii) optionally a genetic marker, e.g. a gene conferring resistance towards an antibiotic, iii) a gene encoding the polypeptide of interest, independently of the host chromosomal replication machinery.

The invention furthermore relates to a method for the generation of a DNA sequence encoding a desired variant of a polypeptide of interest, wherein i) a mutant library is produced by the above method, ii) said library is cultivated under conditions conducive for the expression of said gene of interest to produce polypeptide variants, iii) said variant polypeptides are screened or selected for a desired property, and hosts producing such desired variants identified and isolated, iv) said genetic element in said hosts is sequenced to elucidate the DNA sequence of the mutant gene encoding a desired variant.

and a method for the determination of the DNA sequence encoding a desired variant of a polypeptide of interest, wherein (i) a mutant library is produced by the above method, (ii) said library is cultivated under conditions conducive for the expression of said gene of interest to produce variant polypeptides, (iii) said variant polypeptides are screened or selected for a desired property, and hosts producing desired variants identified and isolated, (iv) said genetic element in said hosts is sequenced to elucidate the DNA sequence of the mutant gene encoding a desired variant.

The screening of the library or the selection of the variants depends on the specific polypeptide and which properties thereof it is desired to improve and/or retain. It is therefore necessary to set up a screening protocol for each case. Such protocols involving a number of assays are described in the literature (Clackson et al., *Nature* 352:624–628, 1991, Bryan, P et al., *Proteins* 1:326–334, 1986).

An elegant approach to the combination of the generation of diversity and the selection of variants with the desired properties would be a combination of the in vivo method of the invention for generating the diversity with a phage display system (Greg Winter, Supra).

A specific example of a polypeptide of interest is the alkaline proteases used in the detergent industry for the removal of proteinaceous stains from fabric. In that case the screening may be performed in actual detergent compositions to investigate properties such as thermal stability, oxidation stability, storage stability, substrate specificity and affinity, stability to non-aqueous solvents, pH profile, ionic strength dependence, catalytic efficiency, and wash performance.

Furthermore the invention relates to a process for the production of a desired polypeptide variant, wherein (i) a DNA sequence encoding a polypeptide of interest that has been determined according to the method above is introduced into a suitable host in a manner whereby it can be expressed in said host, (ii) said host is cultivated under conditions conducive to the expression of said DNA sequence, and (iii) said polypeptide variant is recovered.

Methods for the introduction of the DNA sequence selected into suitable host systems are described in, (Sambrook et al. Molecular Cloning: A Laboratory Manual. Cold Spring Harbor Lab., Cold Spring Harbor, N.Y.).

It is also within the abilities of the skilled person to select suitable growth media and other conditions for the host system selected that are conducive for the expression of the polypeptide variant od interest. Guidance hereto may f. ex. be found in (Sambrook et al., supra).

Also for the recovery of the polypeptide a large number of methods are available for the separation and purification of proteins, e.g. in (Scopes, R. K., Protein Purification (1987), Springer-Verlag)

Lastly, the invention relates to the polypeptides produced by the above method.

DETAILED DESCRIPTION OF THE INVENTION

The invention comprises a method to construct in vivo libraries of variants in a gene of interest. The method involves the use of a genetic element, such as a bacteriophage or a plasmid that is able to replicate independently of the host chromosomal replication system. By the use of the possibility to separate the replication of the host chromosome and the replication of the genetic element (phage/plasmid), it is possible by modifications of one replication system to selectively introduce mutations in the genetic element (phage/plasmid) keeping the chromosome of the host intact. This means that the generation of variation in the gene of interest does not compromise the viability of the host.

DNA replication is a highly accurate process, and the misincorporation rate of the chromosomal replication in *E. coli* has been estimated to be in the order of $10^{-10}$ pr. base pr. round of replication. The base pairing carried out during DNA replication leads to a preference for the polymerase to incorporate the correct base at a certain position, which accounts for approximately $10^5$ of the overall replication fidelity. If an incorrect base has been incorporated, the polymerase will stall and a 3'-5' exonuclease will often remove the 3' misincorporated base. This part denoted proof-reading accounts for approximately $10^2$ of the overall replication fidelity. The repair system of the cell accounts for the last $10^3$ of the fidelity rate.

Replication of the chromosome in *E. coli* is for the most part carried out by DNA polymerase III holoenzyme, which is a multi-protein complex containing 10 different polypeptides including a polymerase (alpha sub-unit, polC gene) and a 3'-5' exonuclease (dnaQ gene).

A further polymerase, DNA polymerase I (DNA pol I, polA gene), contains three different activities, viz. a DNA polymerase activity, a 3'-5' exonuclease activity, and a 5'-3' exonuclease activity despite the fact that it is one single polypeptide. This polymerase has several functions in the cell. Besides DNA repair, DNA pol I is also needed for the chromosomal DNA replication, as it is involved in the assembly of DNA fragments during synthesis of the lagging DNA strand. However, it replicates only a very minor portion of the genome.

This polymerase is furthermore involved in initiation of DNA replication of certain classes of plasmids, e.g. ColEI origin of replication-based plasmids such as pBR322 in *Escherichia coli* and Gram-negative bacteria or pAMβ1 like plasmids in Gram-positive bacteria. Such plasmids may be able to replicate completely through the activity of DNA polymerase I without DNA polymerase III being present in active form, e.g. if this enzyme is dysfunctional due to genetic causes, e.g. temperature sensitive variants at a non-permissive temperature), or under conditions where only limited amounts of DNA Polymerase III are present in the cell.

It is well known that certain mutations lead to a decrease (or an increase) in the fidelity of DNA replication. These mutations have been mapped to reside mainly in polymerases, exonucleases or in elements of the repair system. Unfortunately, most of these mutations alter/impair the fidelity rate for the complete genome present, and such non-targeted mutations are not desirable.

One example of such a mutation could be an inactivation of the 3'-5' exonuclease activity of DNA pol I.

However, according to the invention use is being made of the fact that some elements in the replication system may be temporarily "switched" off, fully or partially, thereby stopping or greatly slowing down the replication of the genome, while replication of certain genetic elements as defined herein is continued.

An *E. coli* strain containing a temperature sensitive DNA pol III (i.e. the polymerase α-sub-unit or another temperature sensitive sub-unit that render the holoenzyme conditionally non-functional), or a function required for initiation of chromosomal replication, such as DnaA, an error prone DNA pol I and a colEI based plasmid containing a gene of interest, is an example of a genetic system according to the invention designed to specifically introduce mutations in the plasmid (and the gene of interest).

In such a system raising the temperature to a non-permissive value will have the effect that DNA pol III ceases to function fully, while the error prone DNA pol I will retain its function and replicates the plasmid with reduced fidelity resulting in mutated copies of the plasmid.

Since the generation of mutations is random, each cell will generate unique mutations and upon lowering the temperature, the temperature sensitive function will become active again, and normal replication of the cells continue.

A variation would be an *E. coli* strain with temperature sensitive alleles of polIII and polI and an inducible expression (by a ts repressor (temperature-sensitive) or by chemical induction) of the error-prone polymerase. At a restrictive temperature and the presence of the inducer mutations will accumulate in the genetic element. At permissive temperature and the absence of the inducer, the complete systems functions as the wild type cell.

Accordingly the invention in its first aspect relates to a method for in vivo production of a mutant library in cells comprising a multitude of mutated genetic elements, wherein an error-prone polymerase is used in each ancestral cell to replicate all or a part of a genetic element comprising
 i) an origin of replication from which replication is initiated,
 ii) optionally a genetic marker, e.g. a gene conferring resistance towards an antibiotic,
 iii) a gene encoding the polypeptide of interest, independently of the host chromosomal replication machinery.

The invention consequently comprises a method for in vivo production of a library in cells comprising a multitude of mutated genetic elements comprising A) providing a cell having
 i) an error-prone polymerase that independently of the chromosomal replication machinery of said cell will replicate all or a part of a genetic element comprising
  a) an origin of replication from which replication is initiated,
  b) optionally a genetic marker, e.g. a gene conferring resistance towards an antibiotic,
  c) a gene encoding the polypeptide of interest, and
 ii) a chromosomal replication machinery that can be reversibly induced to be substantially non-functional,
B) growing such a cell under conditions conducive to its replication to obtain a multitude of ancestral cells,
C) reversibly inducing said chromosomal replication machinery in said ancestral cells to be substantially non-functional for a period of time sufficient to allow for the replication of said genetic element by said error-prone polymerase to generate mutations in said genetic element,
D) reversibly inducing said chromosomal replication machinery in such mutated cells to be substantially functional, and
E) growing such mutated cells under conditions conducive to their replication.

In this context the expression "mutant library" means a set of cells, bacteria or phages (typically $10^5$ to $10^{13}$ cells or phages) that differs with respect to one particular gene encoding a polypeptide of interest. Typically one would like to introduce one or more different amino acid alterations in this particular polypeptide in each member of the library.

In this context the expression "error-prone polymerase" means a polymerase that during DNA replication will incorporate mistakes (one of the wrong nucleotides in a given position or cause a deletion or an insertion of one or several nucleotides) with higher frequency than the polymerase normally used for this purpose (e.g. *E. coli* DNA pol I, *Bacillus subtilis* DNA pol I, T4 DNA polymerase, T7 DNA polymerase).

The expression "ancestral cell" here means such cells wherein no mutations have been introduced. In some embodiments of the invention the mutation cycle may be reiterated, and in that case, such cells that were initially mutated become ancestral cells for the second mutation cycle, etc.

In this context the expression "host chromosomal replication machinery" means the DNA polymerase or DNA polymerase holoenzyme that is mainly responsible for the replication of the host chromosome, e.g. DNA polymerase III in *E. coli*.

In this context the expression "genetic element" means a small (from 1 or 2 kilo bases to 100 kilo bases) entity consisting of RNA or DNA, that is able to replicate independently, i.e. it contains an origin of replication. The genetic element would typically be a bacteriophage, a phagemid, or a plasmid. The genetic element must also according to the invention comprise a gene encoding the polypeptide of interest, and it may further comprise a genetic marker, e.g. a gene conferring resistance towards an antibiotic.

A virus, a retrovirus, or a transposon that is able to replicate independently of the host replication machinery, e.g. retrotransposons could also be used as the "genetic element".

Kim and Loeb (1995, *PNAS* 92: 684–688) have demonstrated that HIV reverse transcriptase (HIV-RT) is able to complement *E. coli* DNA pol I with respect to chromosomal DNA replication and initiation of plasmid DNA replication. The misincorporation rate of HIV-RT (and related retroviral reverse transcriptases) is several orders of magnitude higher than the rate of DNA pol I, i.e. $10^{-3}$ to $10^{-4}$ misincorporations pr. base pr. round of replication. The use of such a polymerase in stead of a mutated error prone *E. coli* DNA pol I in an embodiment of the invention would significantly increase the frequency of replication errors in the system described above.

In a further embodiment of the invention the mutation cycle described above can be reiterated, i.e. the mutagenic polymerase switched on and off several times, thereby generating even more mutants. Such a step could furthermore help the segregation of plasmids if a multicopy plasmid is used as the genetic element.

In certain genetic elements one can envision that only the part of the genetic element located in the vicinity of the origin of replication is replicated by the error-prone polymerase. In such cases, the gene of interest should be situated within this region.

In a specific embodiment of the invention the genetic element is a phage, wherein the gene encoding the polypeptide of interest is positioned at a locus where the polypeptide upon expression is displayed from the surface of the phage, whereby a screening can be performed directly (see Greg Winther, supra). To ensure the correspondence between DNA sequence of the phage and the protein displayed the primary phage stock should be passed through wild type *E. coli*, at low multiplicity of infection, prior to selection or screening.

To further increase the frequency of mutations, the method of the invention comprises embodiments where the method is used in conjunction with a repair deficient host, e.g. mutL, mutS, mutH, or a combination of mutator genome types.

In this context the expression "repair deficient host" means a cell containing one or more alterations in genes encoding proteins known to be directly or indirectly involved in the DNA repair. The result of such mutations is that a higher frequency of introduced mutations (by the polymerases, chemicals, X-ray, UV light, etc.) will not be repaired and will be "permanently" incorporated in the genome, the so called mutator phenotype. Examples of such genes are mutL, mutS, mutH, mutT.

As the genetic element one could as indicated above use a phagemid in stead of a plasmid in order to couple the variant generation to a display system, e.g. M13, fI, fd.

In this context the expression "phagemid" means a plasmid that besides its plasmid origin of replication contains a phage origin of replication. phagemids are dependent of the conditions able to replicate as a plasmid or as a phage (upon infection with a helper-phage).

A phagemid based system would involve the construction of a phagemid containing:

1) a plasmid origin of replication, e.g. ColEI
2) a M13 phage origin of replication
3) a chimeric gene consisting of the gene of interest fused to the gene encoding GIII protein. (Ødrum, P. et al., *Nucl. Acid. Res.* 21: 4491–4498, 1993).

The first step would be the generation of diversity by growing/maintaining an *E. coli* strain transformed with this phagemid as described above. The second step would be the infection with the helper phage in order to create single stranded phagemid that will be packed into phage particles. The phages displaying the variant proteins can then be subjected to a selection procedure.

Also, certain bacteriophages such as T4 or T7 in Eschericia or SPOII and Phi29 in Bacillus contain their own DNA polymerases, and according to the invention one could envision embodiments where the genetic element described above is a bacteriophage containing an error-prone DNA polymerase.

According to the invention the error-prone polymerase is typically selected from the group comprising DNA polymerase I or reverse transcriptases. A preferred error-prone polymerase is a variant of *E. coli* DNA polymerase I or HIV reverse transcriptase.

As a polypeptide of interest a large number is possible, and especially such polypeptides exhibiting biological activities could be mentioned. Among these are enzymes, hormones, receptors, blood-clotting factors, anti-microbial agents, and other such polypeptides important for the prophylaxis and treatment of various disorders and diseases in humans and animals.

Also, enzymes used for industrial purposes could be mentioned. Among such industrial enzymes, enzymes belonging to the groups carbonyl hydrolases, carbohydrases, oxidoreductases, transferases, phytases, anti-microbial polypeptides, oxidoreductases, isomerases, lyases, and ligases.

In this context the expression "carbonyl hydrolase" means enzymes that hydrolyze compounds containing a —C(=O)—X group, where X is oxygen or nitrogen.

Specific classes of enzymes belonging to the group of carbonyl hydrolases are such as hydrolases (lipases) and peptide hydrolases (proteases).

Proteases are here meant as enzymes classified under the Enzyme Classification number E.C. 3.4 in accordance with the Recommendations (1992) of the International Union of Biochemistry and Molecular Biology (IUBMB).

Examples include proteases selected from those classified under the Enzyme Classification (E.C.) numbers:

3.4.11 (i.e. so-called aminopeptidases), including 3.4.11.5 (Prolyl aminopeptidase), 3.4.11.9 (X-pro aminopeptidase), 3.4.11.10 (Bacterial leucyl aminopeptidase), 3.4.11.12 (Thermophilic aminopeptidase), 3.4.11.15 (Lysyl aminopeptidase), 3.4.11.17 (Tryptophanyl aminopeptidase), 3.4.11.18 (Methionyl aminopeptidase).

3.4.21 (i.e. so-called serine endopeptidases), including 3.4.21.1 (Chymotrypsin), 3.4.21.4 (Trypsin), 3.4.21.25 (Cucumisin), 3.4.21.32 (Brachyurin), 3.4.21.48 (Cerevisin) and 3.4.21.62 (Subtilisin);

3.4.22 (i.e. so-called cysteine endopeptidases), including 3.4.22.2 (Papain), 3.4.22.3 (Ficain), 3.4.22.6 (Chymopapain), 3.4.22.7 (Asclepain), 3.4.22.14 (Actinidain), 3.4.22.30 (Caricain) and 3.4.22.31 (Ananain);

3.4.23 (i.e. so-called aspartic endopeptidases), including 3.4.23.1 (Pepsin A), 3.4.23.18 (Aspergillopepsin I), 3.4.23.20 (Penicillopepsin) and 3.4.23.25 (Saccharopepsin); and 3.4.24 (i.e. so-called metallo endopeptidases), including 3.4.24.28 (Bacillolysin).

Examples of relevant subtilisins comprise subtilisin BPN', subtilisin amylosacchariticus, subtilisin 168, subtilisin mesentericopeptidase, subtilisin Carlsberg, subtilisin DY, subtilisin 309, subtilisin 147, thermitase, aqualysin, Bacillus PB92 protease, proteinase K, Protease TW7, and Protease TW3.

Specific examples of such readily available commercial proteases include Esperase®, Alcalase®, Neutrase®, Dyrazym®, Savinase®, Pyrase®, Pancreatic Trypsin NOVO (PTN), Bio-Feed™ Pro, Clear-Lens Pro (all enzymes available from Novo Nordisk A/S).

Examples of other commercial proteases include Maxatase®, Maxacal®, Maxapem® marketed by Gist- Brocades N.V., Opticlean® marketed by Solvay et Cie. and Purafect® marketed by Genencor International.

It is to be understood that also protease variants are contemplated as the polypeptide of interest. Examples of such protease variants are disclosed in EP 130.756 (Genentech), EP 214.435 (Henkel), WO 87/04461 (Amgen), WO 87/05050 (Genex), EP 251.446 (Genencor), EP 260.105 (Genencor), Thomas et al., (1985), Nature. 318, p. 375–376, Thomas et al., (1987), J. Mol. Biol., 193, pp. 803–813, Russel et al., (1987), Nature, 328, p. 496–500, WO 88/08028 (Genex), WO 88/08033 (Amgen), WO 89/06279 (Novo Nordisk A/S), WO 91/00345 (Novo Nordisk A/S), EP 525 610 (Solvay) and WO 94/02618 (Gist-Brocades N.V.).

The activity of proteases can be determined as described in "Methods of Enzymatic Analysis", third edition, 1984, Verlag Chemie, Weinheim, vol. 5.

Lipases are here meant as enzymes classified under the Enzyme Classification number E.C. 3.1.1 (Carboxylic Ester Hydrolases) in accordance with the Recommendations (1992) of the International Union of Biochemistry and Molecular Biology (IUBMB).

Examples include lipases selected from those classified under the Enzyme Classification (E.C.) numbers:

3.1.1 (i.e. so-called Carboxylic Ester Hydrolases), including (3.1.1.3) Triacylglycerol lipases, (3.1.1.4.) Phospholipase $A_2$.

Examples of lipases include lipases derived from the following microorganisms. The indicated patent publications are incorporated herein by reference:

Humicola, e.g. *H. brevispora, H. lanuginosa, H. brevis* var. *thermoidea* and *H. insolens* (U.S. Pat. No. 4,810,414)

Pseudomonas, e.g. *Ps. fragi, Ps. stutzeri, Ps. cepacia* and *Ps. fluorescens* (WO 89/04361), or *Ps. plantarii* or *Ps. gladioli* (U.S. Pat. No. 4,950,417 (Solvay enzymes)) or *Ps. alcaligenes* and *Ps. pseudoalcaligenes* (EP 218 272) or *Ps. mendocina* (WO 88/09367; U.S. Pat. No. 5,389,536).

Fusarium, e.g. *F. oxysporum* (EP 130,064) or *F. solani pisi* (WO 90/09446).

Mucor (also called Rhizomucor), e.g. *M. miehei* (EP 238 023).

Chromobacterium (especially *C. viscosum*)

Aspergillus (especially *A. niger*).

Candida, e.g. *C. cylindracea* (also called *C. rugosa*) or *C. antarctica* (WO 88/02775) or *C. antarctica* lipase A or B (WO 94/01541 and WO 89/02916).

Geotricum, e.g. *G. candidum* (Schimada et al., (1989), *J. Biochem.*, 106, 383–388)

Penicillium, e.g. *P. camembertii* (Yamaguchi et al., (1991), *Gene* 103, 61–67).

Rhizopus, e.g. *R. delemar* (Hass et al., (1991), *Gene* 109, 107–113) or *R. niveus* (Kugimiya et al., (1992) *Biosci. Biotech. Biochem* 56, 716–719) or *R. oryzae*.

Bacillus, e.g. *B. subtilis* (Dartois et al., (1993) *Biochemica et Biophysica acta* 1131, 253–260) or *B. stearothermophilus* (JP 64/7744992) or *B. pumilus* (WO 91/16422).

Specific examples of readily available commercial lipases include Lipolase®, Lipolase™ Ultra, Lipozyme®, Palatase®, Novozym® 435, Lecitase® (all available from Novo Nordisk A/S).

Examples of other lipases are Lumafast™, *Ps. mendocina* lipase from Genencor Int. Inc.; Lipomax™, *Ps. pseudoalcaligenes* lipase from Gist Brocades/Genencor Int. Inc.; *Fusarium solani* lipase (cutinase) from Unilever; Bacillus sp. lipase from Solvay enzymes. Other lipases are available from other companies.

It is to be understood that also lipase variants are contemplated as the polypeptide of interest. Examples of such are described in e.g. WO 93/01285 and WO 95/22615.

The activity of the lipase can be determined as described in "Methods of Enzymatic Analysis", Third Edition, 1984, Verlag Chemie, Weinhein, vol. 4, or as described in AF 95/5 GB (available on request from Novo Nordisk A/S).

In this context the expression "carbohydrase" means all enzymes capable of breaking down carbohydrate chains (e.g. starches) of especially five and six member ring structures (i.e. enzymes classified under the Enzyme Classification number E.C. 3.2 (glycosidases) in accordance with the Recommendations (1992) of the International Union of Biochemistry and Molecular Biology (IUBMB)). Also included in the group of carbohydrases according to the invention are enzymes capable of isomerizing carbohydrates e.g. six member ring structures, such as D-glucose to e.g. five member ring structures like D-fructose.

Examples include carbohydrases selected from those classified under the Enzyme Classification (E.C.) numbers: α-amylase (3.2.1.1) β-amylase (3.2.1.2), glucan 1,4-α-glucosidase (3.2.1.3), cellulase (3.2.1.4), endo-1,3(4)-β-glucanase (3.2.1.6), endo-1,4-β-xylanase (3.2.1.8), dextranase (3.2.1.11), chitinase (3.2.1.14), polygalacturonase (3.2.1.15), lysozyme (3.2.1.17), β-glucosidase (3.2.1.21), α-galactosidase (3.2.1.22), β-galactosidase (3.2.1.23), amylo-1,6-glucosidas,e (3.2.1.33), xylan 1,4-xylosidase (3.2.1.37), glucan endo-1,3-β-D-glucosidase (3.2.1.39), α-dextrin endo-1,6-glucosidase (3.2.1.41), sucrose α-glucosidase (3.2.1.48), glucan endo-1,3-α-glucosidase (3.2.1.59), glucan 1,4-β-glucosidase (3.2.1.74), glucan endo-1,6-β-glucosidase (3.2.1.75), arabinan endo-1,5-α-arabinosidase (3.2.1.99), lactase (3.2.1.108), chitonanase (3.2.1.132) and xylose isomerase (5.3.1.5).

Examples of relevant carbohydrases include α-1,3-glucanases derived from *Trichoderma harzianum*; α-1,6-glucanases derived from a strain of Paecilomyces; β-glucanases derived from *Bacillus subtilis*; β-glucanases derived from *Humicola insolens*; β-glucanases derived from *Aspergillus niger*; β-glucanases derived from a strain of Trichoderma; β-glucanases derived from a strain of *Oerskovia xanthineolytica*; exo-1,4-α-D-glucosidases (glucoamylases) derived from *Aspergillus niger*; αa-amylases derived from *Bacillus subtilis*; α-amylases derived from *Bacillus amyloliquefaciens*; α-amylases derived from *Bacillus stearothermophilus*; α-amylases derived from *Aspergillus oryzae*; α-amylases derived from non-pathogenic microorganisms; α-galactosidases derived from *Aspergillus niger*; Pentosanases, xylanases, cellobiases, cellulases, hemicellulases derived from *Humicola insolens*; cellulases derived from *Trichoderma reesei*; cellulases derived from non-pathogenic mold; pectinases, cellulases, arabinases, hemi-celluloses derived from *Aspergillus niger*; dextranases derived from *Penicillium lilacinum*; endoglucanase derived from non-pathogenic mold; pullulanases derived from *Bacillus acidopullyticus*; β-galactosidases derived from *Kluyveromyces fragilis*; xylanases derived from *Trichoderma reesei*;

Specific examples of readily available commercial carbohydrases include Alpha-Gal™, Bio-Feed™ Alpha, Bio-Feed™ Beta, Bio-Feed™ Plus, Bio-Feed™ Plus, Novozyme® 188, Carezyme®, Celluclast®, Cellusoft®, Ceremyl®, Citrozym™, Denimax™, Dezyme™, Dextrozyme™, Finizym®, Fungamyl™, Gamanase™, Glucanex®, Lactozym®, Maltogenase™, Pentopan™, Pectinex™, Promozyme®, Pulpzyme™, Novamyl™, Termamyl®, AMG (Amyloglucosidase Novo), Maltogenase®, Sweetzyme®, Aquazyme® (all enzymes available from Novo Nordisk A/S). Other carbohydrases are available from other companies.

It is to be understood that also variants of such carbohydrases are contemplated as the polypeptide of interest.

The activity of carbohydrases can be determined as described in "Methods of Enzymatic Analysis", third edition, 1984, Verlag Chemie, Weinheim, vol. 4.

Oxidoreductases are here meant to be enzymes classified under the Enzyme Classification number E.C. 1 (Oxidoreductases) in accordance with the Recommendations (1992) of the International Union of Biochemistry and Molecular Biology (IUBMB).

Examples include oxidoreductases selected from those classified under the Enzyme Classification (E.C.) numbers: Glycerol-3-phosphate dehydrogenase (NAD$^+$)(1.1.1.8), Glycerol-3-phosphate dehydrogenase NAD(P)$^+$ (1.1.1.94), Glycerol-3-phosphate 1-dehydrogenase (NADP) (1.1.1.94), Glucose oxidase (1.1.3.4), Hexose oxidase (1.1.3.5), Catechol oxidase (1.1.3.14), Bilirubin oxidase (1.3.3.5), Alanine dehydrogenase (1.4.1.1), Glutamate dehydrogenase (1.4.1.2), Glutamate dehydrogenase (NAD(P)$^+$) (1.4.1.3), Glutamate dehydrogenase (NADP$^+$) (1.4.1.4), L-Amino acid dehydrogenase (1.4.1.5), Serine dehydrogenase (1.4.1.7), Valine dehydrogenase (NADP$^+$) (1.4.1.8), Leucine dehydrogenase (1.4.1.9), Glycine dehydrogenase (1.4.1.10), L-Amino-acid oxidase (1.4.3.2.), D-Amino-acid oxidase(1.4.3.3), L-Glutamate oxidase (1.4.3.11), Protein-lysine 6-oxidase (1.4.3.13), L-lysine oxidase (1.4.3.14), L-Aspartate oxidase (1.4.3.16), D-amino-acid dehydrogenase (1.4.99.1), Protein disulfide reductase (1.6.4.4), Thioredoxin reductase (1.6.4.5), Protein disulfide reductase (glutathione) (1.8.4.2), Laccase (1.10.3.2), Catalase (1.11.1.6), Peroxidase (1.11.1.7), Lipoxygenase (1.13.11.12), Superoxide dismutase (1.15.1.1)

Said Glucose oxidases may be derived from *Aspergillus niger*.

Said Laccases may be derived from *Polyporus pinsitus, Myceliophtora thermophila, Coprinus cinereus, Rhizoctonia solani, Rhizoctonia praticola, Scytalidium thermophilum* and *Rhus vernicifera*.

Bilirubin oxidases may be derived from *Myrothechecium verrucaria*.

The Peroxidase may be derived from e.g. Soy bean, Horseradish, or *Coprinus cinereus*.

The Protein Disulfide reductase may be any mentioned in any of the DK patent applications no. 768/93, 265/94 and 264/94 (Novo Nordisk A/S), which are hereby incorporated as reference, including Protein Disulfide reductases of bovine origin, Protein Disulfide reductases derived from *Aspergillus oryzae* or *Aspergillus niger*, and DsbA or DsbC derived from *Escherichia coli*.

Specific examples of readily available commercial oxidoreductases include Gluzyme™ (enzyme available from Novo Nordisk A/S). However, other oxidoreductases are available from others.

It is to be understood that also variants of oxidoreductases are contemplated as the polypeptide of interest.

The activity of oxidoreductases can be determined as described in "Methods of Enzymatic Analysis", third edition, 1984, Verlag Chemie, Weinheim, vol. 3.

In this context transferases are enzymes classified under the Enzyme Classification number E.C. 2 in accordance with the Recommendations (1992) of the International Union of Biochemistry and Molecular Biology (IUBMB).

The transferases may be any transferase in the subgroups of transferases: transferases transferring one-carbon groups (E.C. 2.1); transferases transferring aldehyde or residues (E.C. 2.2); acyltransferases (E.C. 2.3); glucosyltransferases (E.C. 2.4); transferases transferring alkyl or aryl groups, other that methyl groups (E.C. 2.5); transferases transferring nitrogenous groups (2.6).

In a preferred embodiment the transferease is a transglutaminase E.C 2.3.2.13 (Protein-glutamine γ-glutamyltransferase).

Transglutaminases are enzymes capable of catalysing an acyl transfer reaction in which a γ-carboxyamide group of a peptide-bound glutamine residue is the acyl donor. Primary amino groups in a variety of compounds may function as acyl acceptors with the subsequent formation of monosubstituted γ-amides of peptide-bound glutamic acid. When the epsilon-amino group of a lysine residue in a peptide-chain serves as the acyl acceptor, the transferases form intramolecular or intermolecular γ-glutamyl-ε-lysyl crosslinks.

Examples of transglutaminases are described in the pending DK patent application no. 990/94 (Novo Nordisk A/S).

The transglutaminase may the of human, aminal (e.g. bovine) or microbially origin.

Examples of such transglutaminases are animal derived transglutaminases, FXIIIa; microbial transglutaminases derived from *Physarum polycephalum* (Klein et al., *Journal of Bacteriology*, 174, p. 2599–2605); transglutaminases derived from Streptomyces sp., including *Streptomyces lavendulae, Streptomyces lydicus* (former *Streptomyces libani*) and Streptoverticillium sp., including *Streptoverticillium mobaraense, Streptoverticillium cinnamoneum,* and *Streptoverticillium griseocarneum* (Motoki et al., U.S. Pat. No. 5,156,956; Andou et al., U.S. Pat. No. 5,252,469; Kaempfer et al., *Journal of General Microbiology*, 137, 1831–1892; Ochi et al., *International Journal of Sytematic Bacteriology*, 44, 285–292; Andou et al., U.S. Pat. No. 5,252,469; Williams et al., *Journal of General Microbiology*, 129, 1743–1813).

It is to be understood that also transferase variants are contemplated as the polypeptide of interest.

The activity of transglutaminases can be determined as described in "Methods of Enzymatic Analysis", third edition, 1984, Verlag Chemie, Weinheim, vol. 1–10.

In this context phytases are enzymes classified under the Enzyme Classification number E.C. 3.1.3 (Phosphoric Monoester Hydrolases) in accordance with the Recommendations (1992) of the International Union of Biochemistry and Molecular Biology (IUBMB).

Phytases are enzymes produced by microorganisms which catalyse the conversion of phytate to inositol and inorganic phosphorus Phytase producing microorganisms comprise bacteria such as *Bacillus subtilis, Bacillus natto* and Pseudomonas; yeasts such as *Saccharomyces cerevisiae;* and fungi such as *Aspergillus niger, Aspergillus ficuum, Aspergillus awamori, Aspergillus oryzae, Aspergillus terreus* or *Aspergillus nidulans,* and various other Aspergillus species).

Examples of phytases include phytases selected from those classified under the Enzyme Classification (E.C.) numbers: 3-phytase (3.1.3.8) and 6-phytase (3.1.3.26).

The activity of phytases can be determined as described in "Methods of Enzymatic Analysis", third edition, 1984, Verlag Chemie, Weinheim, vol. 1–10, or may be measured according to the method described in EP-A1-0 420 358, Example 2 A.

In the present context an anti-microbial polypeptides may be any polypeptide exhibiting anti-microbial activities, such as anti-fungal, anti-bacterial, and/or anti-insecticidal activity.

Such polypeptides may also exhibit other activities such as enzymatic activity.

Examples of anti-microbial polypeptides according to the invention include: fungicidally active polypeptides derived from the mold genus Curvularia described in WO 94/01459 (Novo Nordisk A/S); anti-bacterial polypeptides described in EP 403.458 (Kabigen AB); anti-microbial proteins isolated from the Mirabilis seed, described in WO 92/15691 (Imperial Chem Ind. PLC); anti-bacterial polypeptides isolated from an extract of pig small intestine, described in WO 92/22578 (Boman et al.); polypeptide with yeast lethal action accumulated by yeast of Hansenula spp. as described in JP-60130599; *Phytolacca insularis* antiviral protein, which can be used as an anti-microbial described in U.S. Pat. No. 5,348,865 (Jin Ro LTD.); bacteriolytic enzymes preparations derived from *Nocardiopsis dassonvillei* described in U.S. Pat. No. 5,354,681 (Novo Industri A/S).

Examples of other anti-microbial polypeptides are maganinin, protegrin, defensin, pseudomycin, mutanolysin and N-acetylmuramidase.

The present invention in a further aspect relates to a method for generating a DNA sequence encoding a desired variant of a polypeptide of interest, wherein (i) a mutant library is produced by the above method, (ii) said library is cultivated under conditions conducive for the expression of said gene of interest to produce variant polypeptides, (iii) said variant polypeptides are screened or selected for a desired property, and hosts producing desired variants identified and isolated, (iv) the DNA encoding said variants is isolated.

The present invention in a still further aspect relates to a method for the determination of a DNA sequence encoding a desired variant of a polypeptide of interest, wherein (i) a mutant library is produced as described above, (ii) said library is cultivated under conditions conducive for the expression of said gene of interest to produce variant polypeptides, (iii) said variant polypeptides are screened or selected for a desired property, and hosts producing desired variants identified and isolated, (iv) said genetic element in said hosts is sequenced to elucidate the DNA sequence of the mutant gene encoding a desired variant.

This aspect of the invention can be performed by making dilutions of the library (e.g. in microtiter plates) and culturing these, whereby populations are made each originating from one member of the library, and the variant polypeptide produced from each of the populations screened for the desired properties. Alternatively the library might be plated on agar-plates, containing a desired growth medium that allows for the screening of or selection for desired properties of the variant polypeptide.

If the phage display method is used, the screening or selection is performed directly with the phages.

The criteria used for the selection will vary according to the end use of the polypeptide variant of interest, but properties typically being tested may include solubility and half-life in various media, antigenicity and allergenicity, thermal stability, oxidation stability, storage stability, substrate specificity and affinity, stability to non-aqueous solvents, pH profile, ionic strength dependence, catalytic efficiency, and compatibility with other components of envisaged end products wherein the polypeptide variant will form a part.

For enzymes to be used in detergents further properties to be investigated are, wash performance and compatibility with various surfaces, especially fabrics.

Numerous other criteria could be mentioned.

Upon identification of populations that produce variant polypeptides fulfilling the criteria selected, the DNA encoding the polypeptide variant of interest is isolated and sequenced by use of methods well known in the art.

The invention furthermore comprises a process for the production of a desired polypeptide variant, wherein (i) a DNA sequence determined as indicated above is introduced into a suitable host in a manner whereby it can be expressed in said host, (ii) said host is cultivated under conditions conducive to the expression of said DNA sequence, and (iii) said polypeptide variant is recovered.

The present invention can be used with any cell, especially any microbial cell, but it is often suitable to use a prokaryote, especially a bacterium, preferably of the genus Bacillus, etc.

Among the Bacilli it is preferred to use a strain chosen from the group comprising *B. lentus, B. licheniformis, B. amyloliquefaciens, B. subtilis*, etc.

For some uses it is preferable to use a microbial cell which is a fungus, especially a filamentous fungus, preferably of the genus Aspergillus, Trichoderma, etc.

Among the Aspergilli it is preferable to use a strain chosen from the group comprising *A. oryzae, A. niger, A. awamori*, etc.

Among the Trichoderma it is preferable to use a strain chosen from the group comprising *T. reseei*, etc.

In yet other situations it is more expedient to use a mammalian cell chosen from the group comprising BHK, etc. cells.

The invention should not be construed to be limited to specific examples or embodiments mentioned in the specification above or the following examples.

MATERIALS AND METHODS

EXAMPLES

Example 1

The system used is an *Eschericia coli* host cell, which is characterized by a number of chromosomal mutations:

i) a ts (thermosensitive) mutation in the polC gene (encoding DNA polymerase III, being the main replication polymerase)

ii) a mutation in the polA gene (encoding DNA polymerase I) causing an increased error rate by a reduction in the 3'-5' exonuclease activity.

iii) repair deficiency by the mutL mutation.

The target for the in vivo mutagenesis is plasmid pBR322 (colE1 origin) having either (i) a frame shift mutation, or (ii) a stop codon introduced into the tet gene, encoding a protein conferring resistance towards tetracyclin.

In each case the repair of the mutation leads to a dominant tetracycline resistant phenotype.

pBR322 contains also the bla gene conferring resistance towards ampicillin. The higher mutagenesis frequency at the target region is seen as a higher frequency of tetracycline resistant colonies after plating a culture exposed to "mutation-introduction" conditions.

An *E. coli* culture grown at 37° C. to an optical density of 1 measured at 600 nm is exposed to 2, 4 or 16 hours at restrictive temperature, e.g. 42° C. At these time points dilution series of the cultures are plated on LBagar supplementet with 1) ampicillin (AmpR colonies)
2) tetracycline and ampicillin.(AmpR and tetR colonies)

The ratio of tetracycline resistant colonies to ampicillin resistant colonies indicate the number of cells in the culture that contains one copy of a repaired tet gene, indicated one specific mutagenesis event.

This means, if a clone have become tetracycline resistant, at least one specific mutation has occurred to repair the originally introduced gene defect.

REFERENCES CITED IN THE SPECIFICATION

Greg Winter, *Current methods in Immunology* 5: 253–255, 1993
Griffiths, A. D. et al., 1994, *EMBO J.* 14: 3245–3260.
Clackson et al., *Nature* 352: 624–628, 1991
Bryan, P et al., *Proteins* 1: 326–334, 1986
Sambrook et al. Molecular Cloning: A Laboratory Manual. Cold Spring Harbor Lab., Cold Spring Harbor, N.Y.
Scopes, R. K., Protein Purification (1987), Springer-Verlag
Kim and Loeb (1995, *PNAS* 92: 684–688)
Ørum, P. et al., *Nucl. Acid. Res.* 21: 4491–4498, 1993
EP 130.756 (Genentech), EP 214.435 (Henkel), WO 87/04461 (Amgen), WO 87/05050 (Genex), EP 251.446 (Genencor), EP 260.105 (Genencor), Thomas et al. (1985) *Nature* 318, 375–376, Thomas et al. (1987) *J. Mol. Biol.*, 193 803–813, Russel et al. (1987) *Nature* 328 496–500, WO 88/08028 (Genex), WO 88/08033 (Amgen), WO 89/06279 (Novo Nordisk A/S), WO 91/00345 (Novo Nordisk A/S), EP 525 610 (Solvay) and WO 94/02618 (Gist-Brocades N.V.), U.S. Pat. No. 4,810,414, WO 89/04361, U.S. Pat. No. 4,950,417 (Solvay enzymes), EP 218 272, WO 88/09367, U.S. Pat. No. 5,389,536, EP 130,064, WO 90/09446), EP 238 023, WO 88/02775, WO 94/01541, WO 89/02916, Schimada et al., (1989), *J. Biochem.*, 106, 383–388, Yamaguchi et al., (1991), *Gene* 103, 61–67, Hass et al., (1991), *Gene* 109, 107–113, Kugimiya et al., (1992) *Biosci. Biotech. Biochem* 56, 716–719, Dartois et al., (1993) *Biochemica et Biophysica acta* 1131, 253–260, JP 64/7744992, WO 91/16422, WO 93/01285, WO 95/22615, DK patent applications no. 768/93, 265/94 and 264/94 (Novo Nordisk A/S), DK patent application no. 990/94 (Novo Nordisk A/S), Klein et al., *Journal of Bacteriology*, 174, p. 2599–2605, Motoki et al., U.S. Pat. No. 5,156,956; Andou et al., U.S. Pat. No. 5,252,469; Kaempfer et al., *Journal of General Microbiology*, 137, 1831–1892; Ochi et al., *International Journal of Sytematic Bacteriology*, 44, 285–292; Andou et al., U.S. Pat. No. 5,252,469; Williams et al., *Journal of General Microbiology*, 129, 1743–1813, WO 94/01459 (Novo Nordisk A/S), EP 403.458 (Kabigen AB), WO 92/15691 (Imperial Chem Ind. PLC), WO 92/22578 (Boman et al.), JP-60130599, U.S. Pat. No. 5,348,865 (Jin Ro LTD.), U.S. Pat. No. 5,354,681 (Novo Industri A/S), Methods of Enzymatic Analysis, third edition, 1984, Verlag Chemie, Weinheim, vol. 1–10. AF 95/5 GB (available on request from Novo Nordisk A/S)

What is claimed is:

1. A method for in vivo generation of mutated polynucleotides, the method comprising:
    (a) providing an *E. coli* host cell comprising a polynucleotide encoding an error-prone DNA polymerase I;
    (b) inserting into the host cell of step (a) a DNA polymerase I-dependent plasmid comprising (i) an origin of replication, (ii) a polynucleotide encoding a polypeptide of interest, and optionally (iii) a genetic marker; and
    (c) allowing replication of the plasmid, wherein the error-prone polymerase initiates replication from the origin of replication and replicates the polynucleotide encoding the polypeptide of interest (i), thereby generating mutated polynucleotides.

2. The method of claim 1, further comprising expressing the mutated polynucleotides to generate variant polypeptides of interest.

3. The method of claim 1, wherein the plasmid comprises a ColEI origin of replication.

4. The method of claim 1, wherein the *E. coli* host cell comprises chromosomal replication machinery comprising a temperature sensitive *E. coli* DNA polymerase III.

5. The method of claim 1, wherein the polypeptide of interest is an enzyme.

6. The method of claim 1, wherein the host cell is repair-deficient.

7. The method of claim 1, wherein the host cell further comprises repressible chromosomal replication machinery, and wherein the host chromosomal replication machinery is repressed for a period of time sufficient to allow replication of the plasmid by the error-prone polymerase before replication of the host chromosome.

8. The method of claim 4, wherein the host cell is repair-deficient.

9. The method of claim 5, wherein the enzyme is selected from the group of carbonyl hydrolases, carbohydrases, oxidoreductases, transferases, phytases, ligases, lyases, and anti-microbial polypeptides.

10. The method of claim 6, wherein the repair-deficiency results from the presence of a mutation in one of mutL, mutS, mutH, or a combination thereof.

11. The method of claim 7, further comprising step (d) removing the repression of step (b) wherein the host cells are replicated.

12. The method of claim 8, wherein the repair-deficiency results from the presence of a mutation in one of mutL, mutS, mutH, or a combination thereof.

* * * * *